United States Patent [19]

Sheridan

[11] 4,455,138

[45] Jun. 19, 1984

[54] DENTAL BRACE BRACKET BONDING AND DEBRACKETING TOOL AND METHOD OF USE

[76] Inventor: John J. Sheridan, 1551 Calhoun St., New Orleans, La. 70118

[21] Appl. No.: 431,687

[22] Filed: Sep. 30, 1982

[51] Int. Cl.³ .............................................. A61C 7/00
[52] U.S. Cl. ....................................................... 433/3
[58] Field of Search ..................................... 433/3, 32

[56] References Cited

U.S. PATENT DOCUMENTS 3,821,513  6/1974  Christonsew ........................ 433/32
4,155,164  5/1974  White .................................... 433/3

Primary Examiner—Robert Peshock
Attorney, Agent, or Firm—John M. Harrison

[57] ABSTRACT

A dental brace bracket bonding and debracketing tool which includes a heating device such as a soldering iron, having a heating element tip on one end and an elongated retainer extending from the heating device adjacent the heating element tip and biased outwardly from the tip, the heating element tip and the retainer designed to engage a central slot and flange arms, respectively, of a dental brace bracket in order to bond and debracket the bracket to and from a tooth, respectively. A method of debracketing dental brace brackets from teeth which includes engaging a bracket at at least two points with the heating element tip of a soldering iron or other heating device and a cooperating retainer extending outwardly from the heating device adjacent the heating element tip; applying heat to the bracket in order to alter the bonding material which secures the bracket to the teeth; and removing the bracket from the teeth. A method of bonding dental brace brackets to teeth which includes engaging a bracket at at least at two points with the heating element tip and the retainer; applying a suitable adhesive to the contact surface of the bracket; positioning the bracket in a desired location on a tooth; applying heat to the bracket through the heating element tip, if heat is necessary to aid in hardening the adhesive; and disengaging the heating element tip and the retainer from the bracket.

4 Claims, 6 Drawing Figures

DENTAL BRACE BRACKET BONDING AND DEBRACKETING TOOL AND METHOD OF USE

BACKGROUND OF THE INVENTION

Field of the Invention

This invention relates to the bonding and debracketing of dental brace brackets to and from teeth, respectively, and more particularly, to a dental brace bracket bonding and debracketing tool and method of using the tool to effect the bonding and debracketing operation.

One of the best known techniques for realigning misaligned teeth is by using braces which include multiple bracket members attached to an appropriate location on each tooth with cooperating wire support members or bands attached to the brackets in order to urge the teeth into proper alignment over a period of time. Each of the dental brace brackets comprises a central groove and outwardly extending flanges positioned in oppositely-disposed relationship on one face, and a backing or contact surface on the opposite face in order to permit bonding of the bracket to a tooth. Various adhesives known in the art, including heat-sensitive bonding agents, are used to secure the dental brace brackets to the teeth in a rigid fashion in order to facilitate realignment of the teeth through pressure applied by the bands attached to the brackets.

One of the problems realized in applying dental brace brackets to the respective teeth of a patient is that of aligning the brackets in a proper manner on the teeth to properly orient the bracket grooves in order that the retaining wires or bands attached to the brackets by registration with the grooves exert pressure in the desired direction and intensity to achieve straightening of the teeth in the proper manner. Since the dental brace brackets are quite small, manipulation into proper position on each tooth in the proper location is difficult, and it is preferred to use a tool or device of some description which is capable of engaging and manipulating the bracket in order to accomplish this result. It is also difficult to remove the dental brace brackets without the use of such a tool, and furthermore, heat must generally be applied to the brackets in order to alter the bonding material which secures the brackets to the teeth. Additionally, the heat must be applied in such intensity and in such a manner so as to provide minimum discomfort to the patient, particularly in areas of the mouth where a tooth or teeth may be sensitive due to earlier treatment.

Accordingly, it is an object of this invention to provide a new and improved dental brace bracket bonding and debracketing tool which is characterized by a heating device such as a soldering iron having a shaped heating element tip and a cooperating retainer means extending from the heating device adjacent the heating element tip and biased away from the tip, to facilitate urging of the retainer means toward the heating element tip against the bias, and engaging a dental brace bracket at at least two points for either bonding onto a tooth or debracketing from a tooth, as desired.

Another object of this invention is to provide a new and improved dental brace bracket bonding and debracketing tool which is light in weight, easily manipulated, and which is characterized by a heat source, a cooperating heating element and a heat shield, the heat of which heating element can be carefully controlled as to intensity and the heating element further including a heating element tip and a retainer means extending from the tool in close proximity to the heating element tip and positioned in normally biased relationship away from the heating element tip and capable of being urged toward the heating element tip by the hand of the user to engage a dental brace bracket with the heating element tip and retainer means for positioning the bracket on a tooth, or debracketing the bracket from a tooth, as desired.

Still another object of the invention is to provide a new and improved dental brace bracket bonding and debracketing tool which is characterized by a heating device having a heating element, a heat shield and a heating element tip extending from one end for engagement with the groove of a dental brace bracket, and an elongated retainer extending from the heating device adjacent the heating element tip in normally biased configuration away from the heating element tip for engagement with a flange of the dental brace bracket in order to secure the bracket at at least two points between the retainer and heating element tip for bonding the bracket to a tooth and debracketing the bracket from the tooth, as desired.

Still another object of the invention is to provide a method of bonding dental brace brackets used for supporting metal bands or wires in braces, to teeth, which includes engaging the bracket with a heating element tip extending from a heating device and a cooperating retainer, also extending from the heating device in close proximity to the heating element tip; placing an adhesive material on the back or contact surface of the bracket; positioning the bracket in a desired location on the tooth by manipulating the heating device; applying a specified amount of heat through the heating element tip to activate the bonding agent applied to the bracket under circumstances where hardening of the adhesive is catalyzed by heat; and removing the retainer and heating element tip from the bracket.

Yet another object of the invention is to provide a method for debracketing dental brace brackets used for supporting metal bands in braces, from teeth, which includes the steps of engaging the bracket at at least two points with the heating element tip of a heating device such as a soldering iron and a retaining means cooperating with the heating element tip; applying an appropriate amount of heat to the bracket to alter or loosen the adhesive which bonds the bracket to the tooth; and removing the bracket from the tooth by manipulating the heating device.

SUMMARY OF THE INVENTION

These and other objects of the invention are provided in a dental brace bracket bonding and debracketing tool which, in a preferred embodiment, includes a heating device which is capable of being activated to supply a specific amount of heat to a heating element tip extending from one end of the device, a heat shield cooperating with the heating element and a retainer characterized by a pair of stiff wires connected at one end to the heating device to define a retainer tip projecting from the heating device adjacent the heating element tip. The retainer is normally biased away from the heating element tip to facilitate engagement of the retainer tip and the heating element tip with one set of flanges and the bracket groove, respectively, of a dental brace bracket to support the bracket at at least two points during the bonding or debracketing process. A method of bonding and debracketing a dental brace bracket to and from a tooth, respectively, which, in the bonding process, includes engaging the groove in the bracket with the heating element tip of the heating device and the flanges of the bracket with the retainer tip of the cooperating retainer; applying an adhesive to the mounting or contact surface of the bracket; positioning the bracket at a desired location on the tooth; and applying heat to the bracket in order to catalyze the bonding agent to secure the bracket to the tooth, if a heat-catalyzed adhesive is used. In the debracketing process the dental brace bracket is initially engaged by the heating element tip and retainer, respectively, as described above; a specified amount of heat is applied by operation of the heating device to soften the bonding agent securing the bracket to the tooth; and the bracket is removed from the tooth and supported by the retainer and the heating element tip.

BRIEF DESCRIPTION OF THE DRAWING

The invention will be better understood by reference to the accompanying drawing, wherein.

DESCRIPTION OF THE PREFERRED EMBODIMENTS

Figure 1:
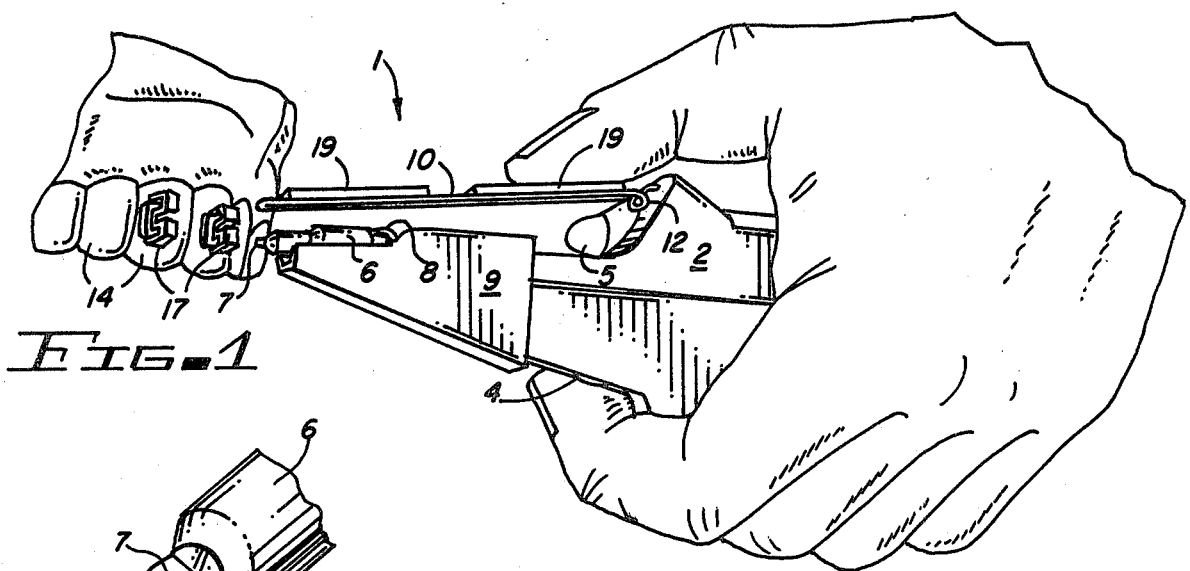
FIG. 1 is a perspective view, partially in section, of the dental brace bracket bonding and debracketing tool in proximity to a dental brace bracket bonded to a tooth.
Figure 2:
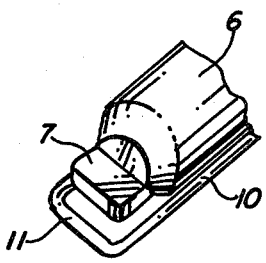
FIG. 2 is a perspective view of a preferred bonding and debracketing tool heating element tip and cooperating retainer and retainer tip.
Figure 4:
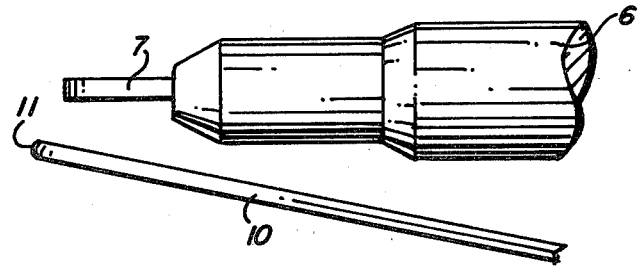
FIG. 4 is a side elevation of the bonding and debracketing tool heating element, heating element tip, retainer and retainer tip, with the heat shield removed.

Referring to FIGS. 1, 2 and 4 of the drawing, the bonding and debracketing tool of this invention is generally illustrated by reference numeral 1, and includes a heating device 2, such as a soldering iron or other device for generating heat, having a switch (not illustrated) and a heat indicator light 4. In a preferred embodiment the bonding and debracketing tool 1 is also provided with a spotlight 5, which illuminates the work area forward of the bonding and debracketing tool 1. A heating element 6 projects from the working end of the heating device 2 by means of heating element connectors 8, which are, in turn, connected to a heating coil (not illustrated) contained within the heating device 2, in conventional fashion. A shaped element tip 7 protrudes from the heating element 6, and in a preferred embodiment of the invention the element tip 7 is flat and is designed for engagement with the groove 15 of a dental brace bracket 13, used to support wires or bands (not illustrated) and provide braces for teeth. A heat shield 9 serves to reduce the heat transfer from the heating element 6 and the element tip 7 to the patient. An elongated retainer 10, provided with retainer grips 19, also projects from the heating device 2 and is further provided with retainer loops 12, to bias the retainer tip 11 of retainer 10 away from the heating element 6, when retainer 10 is in a normally extended configuration. In a preferred embodiment of the invention, and referring specifically to FIGS. 1 and 2, retainer 10 is characterized by a loop of stiff wire shaped to define the retainer tip 11, with the ends of parallel legs shaped by retainer grips 19 and shaped into the loops 12 and attached to the heating device 2. Retainer 10 is slightly longer than the extending end of element tip 7 in order to facilitate engagement of the retainer tip 11 with a dental brace bracket 13 when the retainer 10 is pressed toward heating element 6, as hereinafter described.

Figure 3:
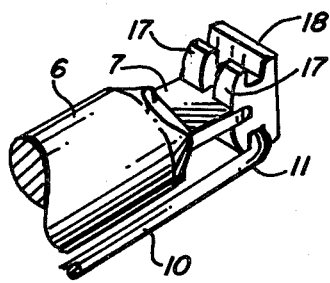
FIG. 3 is a perspective view of the bonding and debracketing tool heating element tip and retainer illustrated in FIG. 2, with the heating element tip and retainer tip engaging a dental brace bracket.
Figure 6:
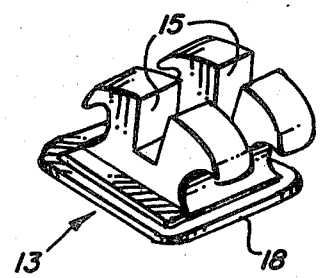
FIG. 6 is a perspective view of a typical dental brace bracket used to support metal wires or bands in braces for teeth.
Figure 5:
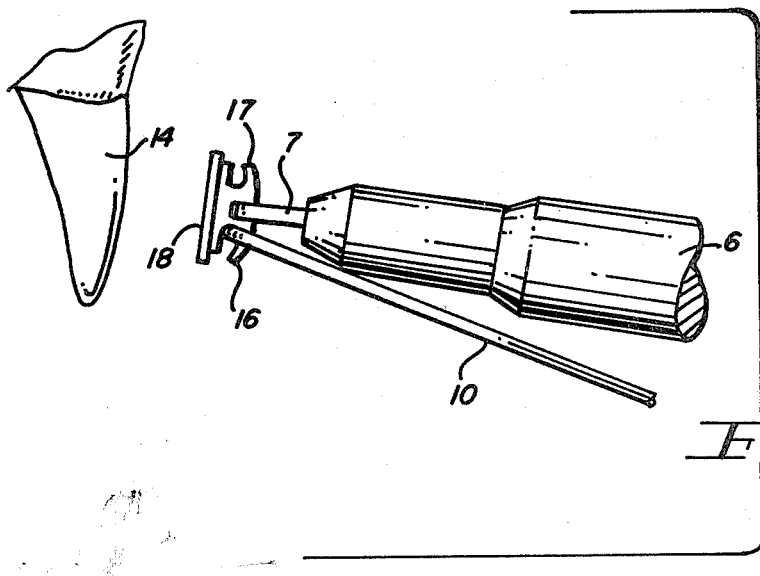
FIG. 5 is a side elevation of the bonding and debracketing tool heating element and retainer, with the heat shield removed and the element tip and retainer tip in position securing a dental brace bracket in close proximity to a tooth.

Referring now to FIGS. 3, 5 and 6 of the drawing the bonding and debracketing tool 1 is utilized in engaging and manipulating a conventional dental brace bracket 13, having a groove 15, and oppositely disposed bottom flanges 16 and top flanges 17, by initially placing the element tip 7 in registration with the groove 15, and simultaneously engaging the retainer tip 11 of retainer 10 with the bottom flanges 16, as illustrated in FIGS. 3 and 5. In this manner, the dental brace bracket 13 is securely held by the bonding and debracketing tool 1 at two points, by means of the retainer tip 11 and the element tip 7, and can be positioned in any desired location on a tooth 14, when a suitable adhesive is applied to the contact surface 18. As illustrated in FIG. 6, in most instances, dental brace brackets 13 are symmetrical in design, since the bottom flanges 16 and top flanges 17 are symmetrical in orientation. Accordingly, the characterization of bottom flanges 16 and top flanges 17 as such is arbitrary, depending upon the choice of flanges for engagement by the retainer tip 11. Furthermore, it will be recognized that substantially any dental brace brackets can be bonded and debracketed to teeth by using the bonding and debracketing tool 1, if the bracket is fitted with flanges or projections for engagement by the element tip 7 and retainer tip 11.

In operation, when it is desired to bond a dental brace bracket 13 to a tooth 14, the dental brace bracket 13 is first supported by the bonding and debracketing tool 1 by initially engaging the element tip 7 of heating element 6 with the groove 15 in the center of a dental brace bracket 13, and the retainer tip 11 with the bottom flanges 16 of the dental brace bracket 13, as illustrated in FIGS. 3 and 5. The retainer tip 11 is engaged with the bottom flanges 16 or the top flanges 17 of the dental brace bracket 13 by initially grasping the heating device 2, placing the thumb on one of the retainer grips 19 or retainer 10, and moving the retainer tip 11 against the bias of retainer loops 12 toward the heating element 7 and beneath the bottom flanges 16 or top flanges 17 with the thumb to grasp the dental brace bracket 13. When the dental brace bracket 13 is thus supported at two points by the bonding and debracketing tool 1, a suitable cement or adhesive is applied to the contact surface 18, and the dental brace bracket 13 is maneuvered into contact with the tooth 14 in the proper position to support suitable connecting wires of the brace system. If the bonding agent is heat-activated or catalyzed, then heat can be applied to element tip 7 through heating element 6 by manipulatiing a switch (not illustrated) and observing the heat indicator light 4. Heat is thus transmitted from the element tip 7 through the dental brace bracket 13 to the bonding agent on the contact surface 18 in order to catalyze hardening of the adhesive. It will be appreciated that the surface of a tooth 14 which is to receive the dental brace bracket 13 may be prepared for bonding by etching or other techniques known to those skilled in the art, and by thoroughly drying the tooth surface, as deemed necessary.

When it is desired to remove a dental brace bracket 13 from a tooth 14, the element tip 7 and retainer tip 11 of retainer 10 are initially engaged as described above and as indicated in FIGS. 3 and 5, and the switch is manipulated to provide heat to heating element 6 and element tip 7 in order to alter or soften the bonding agent or cement on the contact surface 18 and the surface of tooth 14, and permit the dental brace bracket 13 to be removed from the tooth 14.

It will be appreciated by those skilled in the art that the dental brace bracket bonding and debracketing tool of this invention is particularly useful in the application of and removal of dental brace brackets 13 and other applicable orthodontic devices which are used in connection with heat-sensitive bonding agents. Since the heating device 2 is capable of providing heat at varying intensity to the heating element 6 and element tip 7, and the heat shield is in position on the heating element 6, the bonding and debracketing tool 1 is capable of bonding and debracketing the dental brace brackets 13 with little or no discomfort to the patient. Furthermore, the heating device 2 is easily manipulated to engage a dental brace bracket 13 by initially engaging the element tip 7 with the groove 15 of the dental brace bracket 13 and subsequently depressing the retainer 19 to move the retainer tip 11 toward the element tip 7, in order to engage the retainer tip 11 with the bottom flanges 16 or top flanges 17 of the dental brace bracket 13 and position the dental brace bracket 13 in substantially any location on the tooth 14, as heretofore described.

While the preferred embodiments of the invention have been described above, it will be recognized and understood that various modifications may be made therein, and the appended claims are intended to cover all such modifications which may fall within the spirit and scope of the invention.

Having described my invention with the particularity set forth above, what is claimed is:

1. A dental brace bracket bonding and debracketing tool comprising heating means and a heating element projecting from said heating means; an element tip extending from said heating element and shaped to engage the groove in a dental brace bracket having projecting flanges; a resilient member shaped to define a pair of substantially parallel legs, each of said legs having one end secured to said heating means and the opposite end of said leg spaced by a retainer tip extending in close proximity to said element tip and shaped to engage the flanges on one side of the dental brace bracket; and bias means cooperating with said resilient member, whereby said opposite end of said retainer means can be urged into a selected distance from said element tip.

2. The bonding and debracketing tool of claim 1 wherein said bias means is a loop formed in each of said legs.

3. The bonding and debracketing tool of claim 1 wherein said retainer tip extends beyond said element tip when said resilient member is in a position normally spaced from said element tip, and further comprising a heat shield in cooperation with said heating element for reducing heat transfer from said heating element to a patient.

4. The bonding and debracketing tool of claim 1 wherein:
   (a) said bias means is a loop formed in each of said legs; and
   (b) said retainer tip extends beyond said element tip when said resilient member is in a position normally spaced from said element tip, and further comprising a heat shield in cooperation with said heating element for reducing heat transfer from said heating element to a patient.

* * * * *